United States Patent
Stiles

(10) Patent No.: US 6,930,127 B2
(45) Date of Patent: Aug. 16, 2005

(54) VETERINARY TREATMENT OF OPHTHALMIC DISEASE IN ANIMALS USING TOPICAL TACROLIMUS

(75) Inventor: Kris R. Stiles, Phoenix, AZ (US)

(73) Assignee: Eaton Veterinary Laboratories, Inc., Phoenix, AZ (US)

( * ) Notice: Subject to any disclaimer, the term of this patent is extended or adjusted under 35 U.S.C. 154(b) by 0 days.

(21) Appl. No.: 10/465,293

(22) Filed: Jun. 18, 2003

(65) Prior Publication Data
US 2004/0034053 A1 Feb. 19, 2004

Related U.S. Application Data
(60) Provisional application No. 60/403,821, filed on Aug. 15, 2002.

(51) Int. Cl.⁷ .............................................. A61K 31/38
(52) U.S. Cl. ...................................... 514/445; 514/912
(58) Field of Search .............................. 514/291, 443, 514/912, 445

(56) References Cited

U.S. PATENT DOCUMENTS

| | | |
|---|---|---|
| 4,649,047 A | 3/1987 | Kaswan |
| 4,839,342 A | 6/1989 | Kaswan |
| 5,411,952 A | 5/1995 | Kaswan |
| 5,457,182 A | 10/1995 | Wiederrecht et al. |
| 5,624,893 A | 4/1997 | Yanni |
| 6,331,313 B1 | 12/2001 | Wong et al. |
| 6,489,335 B2 | 12/2002 | Peyman |
| 2003/0212090 A1 | 11/2003 | Chen et al. |

OTHER PUBLICATIONS

E.D. Donnenfeld, MD, et al., Cyclosporine provides effective treatment for dry eye, Therapeutic Updates in Ophthalmology, Jul. 1999, pp. 1–3, Irvine, CA.

G.M. Lipper, MD, et al., Recent Therapeutic Advances in Dermatology, JAMA, Jan. 12, 2000, pp 175–177, vol. 283, No. 2, Chicago, IL.

Hampson, et al.; Ocular Discharge and Eyelid Swelling in a Cat; Aust. Vet. J., pp. 172, 185–186, vol. 79, No. 3, Mar. 2001; Brunswick, Vic. 3056.

Christine Dresser, DVM; New Treatment for Dry Eye; The Nova: Rising Star Issue, p. 21, Nov., 2002.

*Primary Examiner*—Zohreh Fay
(74) *Attorney, Agent, or Firm*—Shughart Thomson & Kilroy P.C.; Marcia J. Rodgers

(57) ABSTRACT

A composition and method for veterinary treatment of ophthalmic immune-mediated inflammatory conditions in animals such as conjunctival disorders of the third eyelid, keratoconjunctivitis sicca (KCS), chronic superficial keratitis (CSK), feline eosinophilic keratoconjunctivitis, allergic conjunctivitis, blepharoconjunctivitis, ocular rosacea, viral conjunctivitis, uveitis and phacoanaphylactic endophthalmitis involves the topical administration of tacrolimus to the eye in a pharmaceutically acceptable lubricant vehicle. The composition of the invention includes about 0.00001% to 10.0% tacrolimus by weight in a pharmaceutically acceptable oil-based solution or ointment and may be administered to the third eyelid of an affected animal.

3 Claims, No Drawings

VETERINARY TREATMENT OF OPHTHALMIC DISEASE IN ANIMALS USING TOPICAL TACROLIMUS

CROSS REFERENCE TO RELATED APPLICATION

This application claims priority under 35 U.S.C. § 119(e) based on copending U.S. Provisional Patent Application Ser. No. 60/403,821 filed Aug. 15, 2002 and entitled VETERINARY TREATMENT OF OPHTHALMIC DISEASE IN ANIMALS USING TOPICAL TACROLIMUS.

BACKGROUND OF THE INVENTION

The present invention is broadly concerned with an improved method for treating ophthalmic diseases in veterinary animals. More particularly, it is concerned with a method for topical ophthalmic use of tacrolimus in dogs and cats.

Conjunctivitis, or inflammation of the mobile mucous membrane covering the inner surfaces of the eyelids, is common in all domestic pets. The anatomy of dogs, cats, horses, ruminants and certain other quadrupeds includes a third eyelid, located between the cornea and the lower eyelid in the nasal portion of the lower conjuctival sac. The third eyelid includes a cartilage skeleton, a seromucoid gland and a conjunctival membrane covering both the inner, bulbar and outer, palpebral surfaces. The inner conjunctival surface includes an especially high concentration of lymphocytes that form active follicles when they are stimulated by antigens. For this reason, dogs and cats are particularly subject to development of a conjunctival disorder involving follicle proliferation on the third eyelid. The gland of the third eyelid produces about 50% of the precorneal tear film, so conjunctival disease leading to substantial impairment of the function of the third eye gland can lead to chronic corneal diseases such as keratitis.

When the conjunctival disease process is caused by infection, such as by bacterial pathogens, it is treatable using a therapeutic antibiotic. Chronic superficial keratitis (CSK), chronic keratoconjunctivitis sicca (KCS) and feline eosinophilic keratoconjunctivitis (FEK) are thought to be immune-mediated. CSK is believed to be caused by immune-mediated inflammation of the cornea, exacerbated by external factors such as environmental pollution and exposure to ultraviolet light. KCS may be induced by drugs, surgery, trauma, distemper or poisoning. FEK may be a hypersensitivity reaction similar to allergic diseases in humans which causes inflammatory occlusion of lacrimal ductules. However, most cases are idiopathic, and many of these cases are thought to be associated with autoimmune lymphocyte infiltration and destruction of the gland of the third eyelid and associated reduction in the precorneal tear film.

Certain breeds of dog, such as German shepherds, greyhounds, huskies and dachshunds are particularly subject to a form of interstitial keratitis known as Uberreiter's syndrome, plasma cell conjunctivitis or plasmoma, also called "German Shepherd Pannus" affecting the third eyelid. Kelpies, Australian cattle dogs, border collies, poodle and Labrador retrievers are subject to a similar disease. While some breeds appear to be more prone to CSK, KCS and FEK, these are important diseases found in all breeds of dogs, cats and in a number of other animal species.

Failure to provide adequate and consistent management of these diseases can result in infection, impairment of vision and eventual blindness. Topical cyclosporine has been the preferred therapeutic agent for treatment of chronic KCS in dogs. Although the mechanism of action has not yet been fully elucidated, it is thought to inhibit immune responses and it is known to increase tear production. It has also been employed in the management of CSK in the dog. However, consistent administration of cyclosporine to canines is difficult, because the composition is irritating and causes a burning sensation in the eyes. Even when there is adherence to a therapeutic regimen, the drug is estimated to have an efficacy rate of only about 75–85%.

Preliminary trials of cyclosporine for management of KCS in cats have not been promising. There is some support in the literature for contraindication against treatment of FEK with cyclosporine, because of concern that cyclosporine will potentiate underlying viral keratitis.

Accordingly, there remains a need for an effective, relatively inexpensive topical therapeutic agent for the treatment of conjunctivitis of the third eyelid in dogs as well as cats and which has a relatively low incidence of negative physiological responses.

SUMMARY OF THE INVENTION

The present invention is directed to a composition and method for veterinary treatment of ophthalmic immune-mediated inflammatory conditions in animals such as conjunctival disorders of the third eyelid, keratoconjunctivitis sicca (KCS), chronic superficial keratitis (CSK), feline eosinophilic keratitis (FEK), allergic conjunctivitis, blepharoconjunctivitis, ocular rosacea, viral conjunctivitis, uveitis and phacoanaphylactic endophthalmitis through the topical administration of tacrolimus to the eye in a pharmaceutically acceptable lubricant vehicle.

The composition of the invention includes about 0.00001% to 10.0% tacrolimus by weight in a pharmaceutically acceptable oil-based solution or ointment. The composition may be administered to the third eyelid of an affected animal.

Objects and advantages of this invention will become apparent from the following description wherein are set forth, by way of illustration and example, certain embodiments of this invention.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

A composition and method for treatment of immune-mediated ophthalmic disease in animals in accordance with the invention includes a quantity of tacrolimus intermixed with a quantity of a pharmaceutically acceptable oily solution or ointment. Tacrolimus, or FK-506 is a macrolide immunosuppressant isolated from *Streptomyces tsukubaensis*. Tacrolimus has been used orally, as an immunosuppressant in human organ transplant patients, and topically, for immune-mediated skin conditions such as eczema. Tacrolimus is known to be a potent modulator of the immune response to antigens. It has been demonstrated that tacrolimus inhibits T-lymphocyte activation, although the entire immunosuppression mechanism of action is not-yet known. Tacrolimus also inhibits the transcription for genes that encode IL-3, IL-4, IL-5, GM-CSF and TNF-α, all of which are involved in the early stages of T-cell activation. Tacrolimus has also been shown to inhibit the release of pre-formed mediators from skin mast cells and basophils. Tacrolimus has a lower molecular weight than cyclosporine, is a more effective skin penetrant, and is thought to be up to 100 times more potent than cyclosporine on a per gram basis while exhibiting a relatively low incidence of side effects.

Tacrolimus has a molecular formula of $C_{44}H_{69}NO_{12} \cdot H_2O$, a molecular weight of 822.05 and is available as white crystals or crystalline powder. It is practically insoluble in water, but is soluble in alcohols and some oils. Their intrinsic lubricating qualities make oils and ointments particularly suitable for veterinary use.

Pharmaceutically acceptable oil-based lubricant vehicles may be of animal, vegetable or mineral origin, and may include liquid oils and semi-solid ointments such as corn oil, olive oil, cottonseed oil, sesame oil, canola oil, peanut oil, safflower oil, sunflower oil, dimethyl sulphoxide, alcohols, polyvinyl alcohol, polyoxethylated castor oil, methylcellulose, petrolatum, either in solid form or liquid, as mineral oil and mixtures thereof. The lubricating qualities of such oils serve to increase the surface contact of the therapeutic preparation with the eye surfaces of the animal. Semi-solid ointments such as petrolatum (mineral jelly) are particularly advantageous for veterinary usage, since they generally do not support bacterial growth. It is also foreseen that dimethyl sulphoxide and alcohols, particularly emulsifying alcohols such as polyvinyl alcohol may be employed, either singly or in mixtures with other oil-based lubricant vehicles.

The tacrolimus composition is formulated to include tacrolimus in a concentration of from about 0.00001% to about 10.0% tacrolimus by mass along with an inert, pharmaceutically acceptable lubricant vehicle. The composition may also include a wide range of additives to facilitate application, to control release, to stabilize the composition and for other reasons well known in the art.

The veterinary composition of the present invention may be employed efficaciously to treat ophthalmic disease in virtually all veterinary animals including dogs and cats, as well as people.

In the use of a liquid tacrolimus composition, the lower eyelid is restrained with the hand holding the head of the animal, such as a, dog or cat. The upper lid is retracted with the edge of the palm. A container of the therapeutic tacrolimus composition is held 2 or 3 centimeters from the eye and a drop of the composition is instilled in the eye. In preferred embodiments, the composition is administered on or adjacent to the third eyelid of the animal.

Ointment-type compositions are similarly administered, except that the lower lid is pulled downwardly and outwardly to expose the conjunctiva and form an area for receiving the ointment. A small quantity of the therapeutic ointment is taken up on a cotton swab or finger and placed in the receiving area, preferably on or adjacent to the third eyelid. The two outer lids may be manually closed and massaged lightly to distribute the ointment over the eye and all lid surfaces.

EXAMPLE 1

Clinical Trial of Topical Tacrolimus in Treatment of Canine Keratoconiuncitivitis Sicca A population of canines with keratoconjunctivitis sicca was subject to a method of treatment with a topical tacrolimus solution in order to evaluate the therapeutic effectiveness of the drug.

Materials 0.02% tacrolimus was prepared in a physiologically acceptable ointment base.

0.02% tacrolimus was prepared in a physiologically acceptable oil base.

Schirmer Tear Test strips were employed to measure tearing.

Petrolatum eye ointment was used for patient comfort.

Commercial eyewash was used as a cleaning solution.

Subjects

The test group consisted of 26 dogs of various breeds from different geographic areas. All dogs exhibited clinical signs of KCS and lowered Schirmer Tear Test (STT) wetting values in a 60 second test.

Methods 24 dogs were administered a dose of tacrolimus in either ointment or oil base twice daily in both eyes for 30 days. 2 dogs received the same treatment in only one eye. Petrolatum ointment was administered to some dogs as necessary for comfort. Debris was flushed from the eyes as necessary using a commercial eyewash preparation. The eyes were examined and observations recorded at days 7–14 and again at 21–30 days during treatment.

Results

96% of the treated eyes exhibited improvement. 92% of treated eyes exhibited improved STT values. None of the subjects exhibited signs of ocular irritation. Additional effects noted included: reduction in inflammation of the conjunctiva and reduction in corneal scarring and pigmentation. Tacrolimus was not an effective treatment for all of the dogs, but was effective in some dogs for whom cyclosporine treatment had previously failed.

It is to be understood that while certain forms of the present invention have been illustrated and described herein, it is not to be limited to the specific forms or arrangement of parts described and shown.

What is claimed and desired to be secured by Letters Patent is as follows:

1. A method of treating pannus in canines having said disease and comprising the steps of:

a) providing a quantity of a composition consisting essentially of an effective amount of tacrolimus in a pharmaceutically acceptable non-aqueous lubricant vehicle; and b) administering a quantity of said composition to the third eyelid of an affected canine.

2. The method as set forth in claim 1, wherein:

a) said tacrolimus is present in a concentration of from about 0.00001% to about 10.0% by weight.

3. The method as set forth in claim 1, wherein said lubricating vehicle is selected from the group consisting essentially of corn oil, olive oil, mineral oil, cottonseed oil, sesame oil, canola oil, peanut oil, safflower oil, sunflower oil, polyoxethylated castor oil, petrolatum, mineral oil or mixtures thereof.

* * * * *